United States Patent [19]

Preston

[11] Patent Number: 5,576,464
[45] Date of Patent: Nov. 19, 1996

[54] REMOVAL OF METHANOL FROM METHYL TERTIARY BUTYL ETHER

[75] Inventor: Kyle L. Preston, Port Arthur, Tex.

[73] Assignee: Texaco Chemical Inc., White Plains, N.Y.

[21] Appl. No.: 512,585

[22] Filed: Aug. 8, 1995

[51] Int. Cl.⁶ .................................................. C07C 41/09
[52] U.S. Cl. ........................ 568/697; 568/698; 568/699
[58] Field of Search ................................. 568/697, 698, 568/699

[56] References Cited

U.S. PATENT DOCUMENTS 5,387,721   2/1995   Kruse et al. ............................. 568/697

*Primary Examiner*—Gary Geist
*Assistant Examiner*—Dwayne C. Jones
*Attorney, Agent, or Firm*—James L. Bailey; Kenneth R. Priem; Cynthia L. Hunter

[57] ABSTRACT

MTBE, prepared by reacting MeOH with TBA to form a primary etherification reaction product, is distilled in a first distillation column to provide a first lower boiling distillation fraction comprising methyl tertiary butyl ether, isobutylene, methanol, dimethyl ether, and the first lower boiling fraction is water washed to provide an overhead extract that is distilled in a second distillation column to provide a second lower boiling distillation fraction comprising isobutylene, dimethyl ether and water, which is dewatered to provide a feed fraction comprising isobutylene and dimethyl ether that is reacted with less than an equivalent amount of MeOH to provide a secondary reaction product comprising MTBE, less than 0.5 wt. % of MeOH, isobutylene and contaminants including TBA and dimethyl ether, and the secondary reaction product is recycled to the second distillation column.

3 Claims, 1 Drawing Sheet

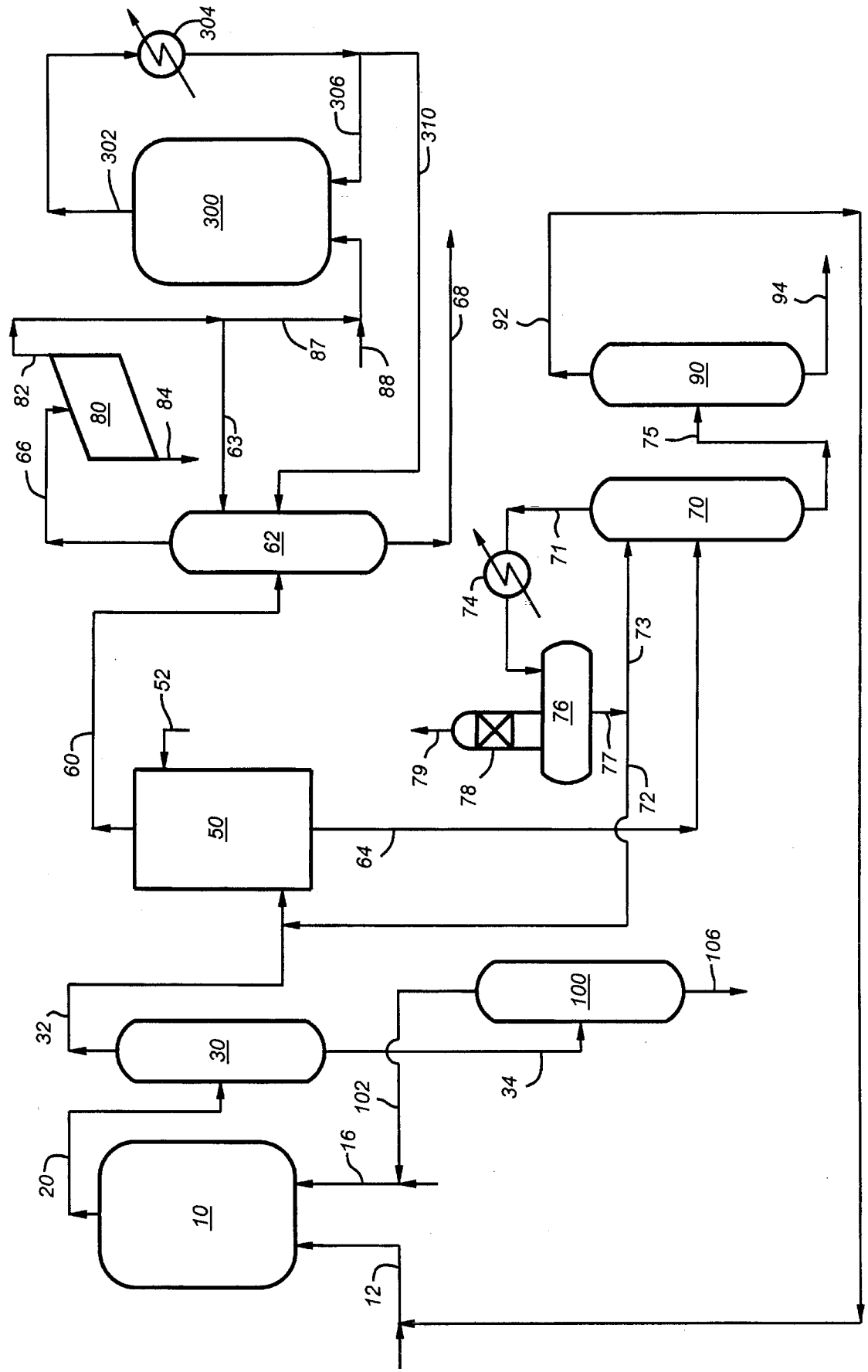

REMOVAL OF METHANOL FROM METHYL TERTIARY BUTYL ETHER

BACKGROUND OF THE INVENTION

1. Technical Field of the Invention

This invention relates to a method for the manufacture of methyl tertiary butyl ether by the sequential reaction of tertiary butyl alcohol and isobutylene with methanol and to the removal of methanol from the methyl tertiary butyl ether. More particularly, this invention relates to a method for the manufacture of methyl tertiary butyl ether by the sequential reaction of tertiary butyl alcohol and isobutylene with methanol and to the removal of methanol from the methyl tertiary butyl ether formed by the reactions.

2. Prior Art

Kruse et al. U.S. Pat. No. 5,243,091 discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol, isobutylene and water, wherein the reaction product is separated in a distillation zone into a lighter fraction comprising methanol, isobutylene and methyl tertiary butyl ether and a heavier fraction comprising tertiary butyl alcohol, methanol and water, and wherein the lighter fraction is charged to a finishing reactor wherein isobutylene and methanol are reacted to form additional methyl tertiary butyl ether.

In copending coassigned application Ser. No. 08/147,508, filed Nov. 5, 1993 now U.S. Pat. No. 5,395,982 and entitled "Continuous Isobutylene Assisted Aqueous Extraction of Methanol from Methyl Tertiary Butyl Ether" there is disclosed a method for the continuous purification of methyl tertiary butyl ether contaminated with isobutylene, methanol and water, by the sequential steps of water extraction in the presence of an added isobutylene stripping agent to form an extract and a raffinate, distillation of the raffinate to form a heavier product methyl tertiary butyl ether fraction and a lighter isobutylene fraction from which isobutylene is recovered for recycle to the extraction zone.

In the process of Kruse et al. U.S. Pat. No. 5,243,091, tertiary butyl alcohol is reacted with methanol to provide a primary reaction product that is distilled to provide a methyl tertiary butyl ether distillation fraction that is contaminated with methanol and isobutylene. The methyl tertiary butyl ether distillation fraction is reacted with methanol to provide additional methyl tertiary butyl ether, and the methanol-contaminated isobutylene reaction product is washed with water to remove the methanol and to forman aqueous raffinate, which contains both methyl tertiary butyl ether and isobutylene that is distilled in a drying distillation column to separate the methyl tertiary butyl ether from the isobutylene and water.

In copending coassigned Preston et al. U.S. patent application Ser. No. 08/345,663, filed Nov. 28, 1994, and entitled "Sequential Reaction of TBA with Isobutylene and Methanol" (D#82,040), a process is disclosed wherein tertiary butyl alcohol and methanol are reacted, as in Kruse et al. to form a primary reaction product. Preston et al. water wash the methyl tertiary butyl ether distillation fraction, distill the raffinate from the water washing step to separate the methyl tertiary butyl ether from isobutylene and water and to forman isobutylene fraction that is reacted with methanol in a secondary reaction zone to form a secondary etherification reaction product comprising water, methanol, isobutylene, dimethyl ether, tertiary butyl alcohol and methyl tertiary butyl ether.

Gupta U.S. Pat. No. 5,292,964 also discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol and water, wherein the reaction product is separated in a distillation zone into a lighter fraction comprising substantially anhydrous methanol and methyl tertiary butyl ether and a heavier fraction comprising tertiary butyl alcohol, methanol and water, and wherein the lighter fraction is charged to a finishing reactor wherein the methanol is reacted with isobutylene to form additional methyl tertiary butyl ether.

In U.S. Pat. No. 4,144,138 (1979) to Rao et al., there is disclosed a method for recovering methyl tertiary butyl ether from an etherification reaction effluent by azeotropic distillation to recover a methanol-ether azeotrope overhead which is water-washed to give pure ether raffinate, the latter being azeotropically distilled to yield an ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

BACKGROUND INFORMATION

Methyl tert-butyl ether is finding increasing use as a blending component in high octane gasoline as the current gasoline additives based on lead and manganese are phased out. Current commercial processes for the manufacture of methyl tert-butyl ether are based upon the liquid-phase reaction of isobutylene and methanol catalyzed by a cationic ion-exchange resin.

With the expanding use of MTBE as an acceptable gasoline additive, a growing problem is the availability of raw materials. Historically, the critical raw material is isobutylene (Oil and Gas J., Jun. 8, 1987, P. 55). It would be advantageous, therefore, to have a process to make MTBE that does not require isobutylene as a starting material. It would be advantageous to have an efficient process for making MTBE by reaction of methanol with tertiary butyl alcohol, since t-butanol (TBA) is readily available commercially through isobutane oxidation.

It is known to react methanol with tertiary butyl alcohol in the presence of a catalyst in order to product methyl tertiary butyl ether.

Two of the principal by-products formed during the reaction of the methanol with the tertiary butyl alcohol are water and isobutylene. The separation of MTBE from methanol during the recovery of purified MTBE presents a serious problem.

In U.S. Pat. No. 4,820,877, separation of methanol from MTBE is accomplished by using a refinery fuel gas to enhance the separation of methanol into the overhead stream of a distillation column.

In U.S. Pat. No. 4,814,517, separation of methanol from MTBE is accomplished by using a silica gel to preferentially adsorb methanol from an MTBE stream and by periodically regenerating the silica gel.

In U.S. Pat. No. 4,798,674, separation of methanol from MTBE is accomplished by using a membrane of crosslinked polyvinyl alcohol or a quaternary ammonium ion resin. Methanol preferentially permeates through the membrane increasing the MTBE concentration of the charge liquid.

In U.S. Pat. No. 4,759,850, separation of methanol from MTBE is accomplished by reverse osmosis.

In U.S. Pat. No. 4,440,963, separation of methanol from MTBE is accomplished by adding an agent such as 2-methyl pentane or Freon 113 to form an azeotrope with methanol. This azeotrope is recovered overhead giving a methanol-free MTBE bottoms product.

As recognized by Rao et al. in U.S. Pat. No. 4,144,138, isobutylene is formed as a by-product when methanol is reacted with tertiary butyl alcohol. In accordance with the Rao process, the isobutylene is separated from the reaction product in an initial azeotropic distillation step as a noncondensable gas. Rao teach that part of the isobutylene may be flashed from the reaction product for recycle, depending upon purity.

SUMMARY OF THE INVENTION

The present invention is directed to a process for the preparation of methyl tertiary butyl ether by the sequential reaction of tertiary butyl alcohol and isobutylene with methanol and to the removal of methanol from methyl tertiary butyl ether formed by the reactions, whereby a methyl tertiary butyl ether product of improved purity is obtained, the methyl tertiary butyl ether product being characterized by very low levels of water, methanol and tertiary butyl alcohol contamination.

In the process of copending coassigned Preston et al. U.S. patent application Ser. No. 08/345,663, filed Nov. 28, 1994, and entitled "Sequential Reaction of TBA with Isobutylene and Methanol," supra isobutylene recovered from the primary reaction of tertiary butyl alcohol is reacted with methanol in a secondary reactor to form additional methyl tertiary butyl ether. Preston et al. teach that methanol may be reacted with isobutylene in the presence of a solid resin etherification catalyst in the secondary reactor in the molar ratio of about 0.5 to about 3 moles of methanol per mol of isobutylene under reaction conditions including a temperature of about 20° to about 160° C., a pressure of about 50 to 500 psia and a flow rate of about 0.5 to about 10 volumes of feed per volume of solid resin etherification catalyst per hour and that the secondary reaction product will comprise not only methyl tertiary butyl ether but also unreacted methanol and isobutylene and that contaminants such as tertiary butyl alcohol and dimethyl ether will also be present.

As a consequence, the additional methyl tertiary butyl ether must be separated from the other reaction products. The separation of methanol from methyl tertiary butyl ether by distillation presents a special problem because methanol and methyl tertiary butyl ether form an azeotrope. Preston et al. solve the problem of the methanol/methyl tertiary butyl ether azeotrope in the purification of methyl tertiary butyl ether formed in their secondary reactor by recycling their secondary reaction product to the water-washing tower used in the removal of methanol from methyl tertiary butyl ether formed in the primary reaction product.

Although the Preston et al. process provides generally satisfactory results, there is a need for improvement, especially insofar as the purification of the secondary reaction product is concerned.

In accordance with the process of the present invention, this and related problems are substantially resolved by reacting isobutylene with less than a stoichiometric amount of methanol, namely about 0.3 to about 0.8 mols of methanol per mol of isobutylene, under moderate reaction conditions including a temperature of about 35° to about 100° C. a pressure of about 150 to 250 psia and a flow rate of about 0.5 to about 10 volumes of feed per volume of solid resin etherification catalyst. It has been discovered in accordance with the present invention that the secondary reaction product prepared in this fashion will contain less than about 0.5 wt. % of methanol.

More particularly, the present invention is directed to a method for the continuous preparation of methyl tertiary butyl ether (MTBE) from tertiary butyl alcohol (TBA), isobutylene (IBTE) and methanol (MeOH), which comprises the steps of:

a) passing a feed mixture comprising tertiary butyl alcohol and methanol through a methyl tertiary butyl ether etherification reaction zone containing a bed of a TBA/MeOH etherification catalyst under etherification reaction conditions to form a primary etherification reaction product comprising unreacted methanol, unreacted tertiary butyl alcohol, water, isobutylene and methyl tertiary butyl ether;

b) distilling the primary etherification reaction product in a first distillation column to provide a first lower boiling (lighter) distillation fraction comprising methyl tertiary butyl ether, isobutylene, methanol, dimethyl ether, and water and a first higher boiling (higher) distillation fraction comprising tertiary butyl alcohol, methanol and water;

c) charging the first lower boiling (lighter) distillation fraction to a methanol solvent extraction zone and contacting it therein with water to provide an overhead extract comprising isobutylene, dimethyl ether, water and methyl tertiary butyl ether, and a raffinate comprising methyl tertiary butyl ether, methanol, dimethyl ether and water;

d) charging the extract to a second distillation column and separating it therein into a second lower boiling (lighter) distillation fraction comprising isobutylene, dimethyl ether and water and a second higher boiling (heavier) distillation fraction comprising methyl tertiary butyl alcohol;

e) separating the second lower boiling (lighter) distillation fraction into a feed fraction comprising isobutylene and dimethyl ether and a water fraction;

f) charging the feed fraction and methanol to a secondary reactor containing a bed of a solid resin etherification catalyst together with methanol in the molar ratio of about 0.3 to about 0.8 mols of methanol per mol of isobutylene, under reaction conditions including a temperature of about 35° to about 100° C. a pressure of about 150 to 250 psia and a flow rate of about 0.5 to about 10 volumes of feed per volume of solid resin etherification catalyst per hour to thereby provide a secondary reaction product comprising methyl tertiary butyl ether, less than 0.5 wt. % of methanol, isobutylene and contaminants including tertiary butyl alcohol and dimethyl ether; and g) recycling said secondary reaction product to said second distillation column.

A preferred embodiment of the present invention comprises the steps of:

a) charging a mixture of methanol and tertiary butyl alcohol in the molar ratio of about 0.5 to 4 moles of methanol per mol of tertiary butyl alcohol to an etherification reaction zone containing a bed of an etherification catalyst under reaction conditions including a pressure of about 30 to about 500 psia, a temperature of about 80° to about 140° C. and a flow rate of about 0.5 to about 20 volumes of feed mixture per volume of etherification catalyst per hour to thereby form a primary reaction product comprising unreacted methanol, unreacted tertiary butyl alcohol, water, dimethyl ether, isobutylene and methyl tertiary butyl ether;

b) charging the primary reaction product to a first methyl tertiary butyl ether recovery distillation zone and separating it therein into a first lower boiling (lighter) distillation fraction comprising isobutylene, dimethyl ether, methanol, water and methyl tertiary butyl ether and a first higher boiling (heavier) distillation fraction comprising methanol, tertiary butyl alcohol and water;

c) charging the first lower boiling (lighter) distillation fraction to a methanol solvent extraction zone and countercurrently contacting the first lower boiling (lighter) distillation fraction therein with water in the ratio of about 1 to about 10 volumes of the first lower boiling (lighter) distillation fraction per volume of water per hour under extraction conditions including a temperature of about 20° to about 60° C. and a pressure of about 50 to about 500 psia to thereby provide an overhead extract comprising isobutylene, dimethyl ether (DME), water and methyl tertiary butyl ether and a raffinate comprising methanol, MTBE, DME and water;

d) charging the extract to a second methyl tertiary butyl ether purification distillation zone and separating it therein into a second lower boiling (lighter) distillation fraction comprising isobutylene, DME and water and a second higher boiling (heavier) distillation fraction consisting essentially of substantially anhydrous methyl tertiary butyl ether substantially free from tertiary butyl alcohol;

e) charging the second distillation fraction to a decantation separation zone and separating it therein into an isobutylene DME fraction and a water fraction;

f) continuously charging at least a portion of the isobutylene DME fraction and added methanol to an isobutylene conversion reaction zone in the molar ratio of about 0.3 to about 0.8 moles of methanol per mol of isobutylene and contacting them therein with a solid resin etherification catalyst under conversion conditions including a temperature of about 35° to about 120° C., a pressure of about 150 to about 250 psia and a flow rate of about 0.5 to about 4 volumes of isobutylene fraction per volume of solid resin etherification catalyst per hour to thereby convert a portion of the isobutylene and a portion of the methanol to methyl tertiary butyl ether and form an isobutylene conversion product comprising methyl tertiary butyl ether, unreacted isobutylene, DME, less than 0.5 wt. % of unreacted methanol, tertiary butyl alcohol and water;

g) continuously charging the extract to a third methyl tertiary butyl ether distillation zone and separating it therein into a third lower boiling (lighter) azeotrope distillation fraction comprising methyl tertiary butyl ether, DME and isobutylene and a third higher boiling (heavier) distillation fraction comprising methanol and water;

h) charging the third higher boiling (heavier) distillation fraction to a fourth methanol recovery distillation zone and separating it therein into a fourth lower boiling (lighter) distillation fraction comprising methanol and a fourth higher boiling (heavier) distillation fraction comprising water;

i) charging the second distillation fraction to a fifth tertiary butyl alcohol recovery distillation zone and separating it therein into a fifth lower boiling (lighter) distillation fraction comprising methanol, tertiary butyl alcohol and water and a fifth higher boiling (heavier) distillation fraction comprising a water fraction; and j) recycling said isobutylene conversion product to said second distillation zone.

The third lower boiling (lighter) MTBE fraction may be recycled to the methanol solvent extraction zone. The fourth lower boiling (lighter) methanol fraction and the fifth lower boiling (lighter) tertiary butyl alcohol fraction may be recycled to the primary methyl tertiary butyl ether etherification reaction zone.

Tertiary butyl alcohol is frequently produced by the thermal or catalytic decomposition of tertiary butyl hydroperoxide. Tertiary butyl alcohol formed in this fashion will normally contain a minor amount of peroxide contaminants such as tertiary butyl hydroperoxide, ditertiary butyl peroxide, allyl tertiary butyl peroxide, etc. Normally, the peroxide contaminants in the tertiary butyl alcohol will remain as contaminants in the etherification reaction zone reaction product. Preferably, therefore, the tertiary butyl alcohol feedstock is charged to a suitable peroxides decomposition zone, such as a thermal peroxides decomposition zone, where the peroxide contaminants are thermally decomposed under decomposition conversion conditions including a temperature of about 100° to about 200° C., a pressure of about 80 to about 500 psia and a flow rate of about 0.5 to about 4 volumes of tertiary butyl alcohol per volume of said solid peroxide decomposition catalyst per hour to thereby decompose the peroxide contaminants and form a tertiary butyl alcohol effluent substantially completely free from peroxide contaminants.

DETAILED DESCRIPTION OF THE PRESENT INVENTION

The Etherification Reaction Catalyst

In accordance with the MTBE manufacture and purification method of the present invention, an etherification reaction zone containing a bed of etherification catalyst is utilized. A wide variety of etherification catalysts can be used for this purpose. For example, a solid resin etherification catalyst may be used for this purpose, such as a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138. A solid acidic catalyst may be used, such as Kieselguhr impregnated with a phosphoric acid as disclosed in Frolich U.S. Pat. No. 2,282,469; also, zeolites as disclosed in Japanese Patent 0007432, aluminosilicate zeolites as disclosed in Chang et al. U.S. Pat. No. 4,058,576, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc.

The reaction conditions to be utilized when reacting methanol with tertiary butyl alcohol in the presence of an etherification catalyst of the type disclosed in the prior art include a reaction temperature of about 90° to about 140° C. a pressure of about 30 to about 500 psia and a flow rate of about 0.5 to about 20 volumes of feed per volume of etherification catalyst per hour.

The Solid Resin Etherification Catalyst

In accordance with the present invention, methyl tertiary butyl ether and isobutylene are recovered from the primary reaction product and the recovered isobutylene and methanol are brought into contact with a solid resin etherification catalyst in order to convert a significant portion of the isobutylene and methanol to methyl tertiary butyl ether.

Any suitable solid resin etherification catalyst may be used for this purpose, such as a strongly acidic ion exchange resin consisting essentially of sulfonated polystyrene, such a divinyl benzene crosslinked polystyrene matrix containing from about 0.5 to about 20% of copolymerized divinyl benzene. Resins of this nature of manufactured and sold commercially under various trade names such as "Dowex 50", "Nalcite HCR" and "Amberlyst 15". The use of catalyst of this nature is disclosed, for example, in Rao U.S. Pat. No. 4,144,138.

The isobutylene and methanol are brought into contact with a solid resin etherification catalyst in an isobutylene conversion reaction zone under conversion conditions including, for example, a temperature of about 35° to about 100° C., a pressure of about 150 to about 250 psia and a flow rate of about 1 to about 10 volumes of isobutylene/methanol feed per volume of solid resin etherification catalyst per hour.

BRIEF DESCRIPTION OF THE DRAWING

The drawing is a schematic flow sheet with conventional parts omitted showing the general reaction and recovery sequence of the present invention for the manufacture and purification of methyl tertiary butyl ether.

DESCRIPTION OF THE PREFERRED EMBODIMENT

Turning now to the drawing, there is shown a schematic flow sheet illustrating a preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with the present invention, there is provided a primary etherification reaction zone 10 containing a bed of a solid etherification catalyst, such as a solid resin etherification catalyst (e.g., a strongly acidic ion exchange resin of the type disclosed above, such as "Dowex 50", "Nalcite HCR" and "Amberlyst 15").

A substantially peroxide-free tertiary butyl alcohol feedstock is continuously charged to the etherification reaction zone 10 by a line 12. Methanol is charged to the etherification reaction zone 10 by a line 16. The flow of methanol and tertiary butyl alcohol to the etherification reaction zone 10 is regulated so that a molar excess of methanol is present such as, for example, a molar ratio of about 1.1 to about 3 moles of methanol per mol of tertiary butyl alcohol.

Within the etherification reaction zone 10, the feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., a still more preferably from about 90° to about 130° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

Within the etherification reaction zone 10, methanol will exothermically react with the tertiary butyl alcohol to form methyl tertiary butyl ether which will be contained in a reaction product discharged from the etherification reaction zone 10 by way of a line 20 leading to a first methyl tertiary butyl ether (MTBE) distillation zone 30.

As a specific example, when the solid etherification catalyst is a sulfonic acid resin such as Amberlyst 15 and when the molar ratio of methanol to tertiary butyl alcohol in the feed mixture charged to the etherification reaction zone 10 by the line 14 is within the ratio of about 2.0 moles of methanol per mole of tertiary butyl alcohol, and the reaction is conducted at a temperature of about 100° C. at a feed rate of about 2.0 volumes of feed mixture per volume of catalyst per hour, a representative etherification reaction product will have the composition in part shown by the following table:

| ETHERIFICATION REACTION PRODUCT | |
|---|---|
| Component | wt. % |
| Water | 14.0 |
| Methanol | 27.6 |
| Isobutylene | 3.0 |
| TBA[1] | 14.1 |
| MTBE[2] | 34.5 |
| Other[3] | 6.8 |

[1]Tertiary butyl alcohol
[2]Methyl tertiary butyl ether
[3]Includes the acetone, propanol, ditertiary butyl peroxide, tertiary butyl formate, etc., initially present in the tertiary butyl alcohol feedstock and DME (formed from methanol).

The etherification reaction product charged to the first MTBE distillation zone 30 by way of the charge line 20 is fractionated therein under distillation conditions including a liquid reflux temperature of about 25° to about 100° C., and more preferably about 30° to about 80° C., a reboiler temperature of about 80° to about 115° C., and more preferably from about 95° to about 105° C., and a pressure of about 15 to about 60 psia, the distillation condition being selected such that substantially all of the MTBE in the etherification reactor 10 is taken overhead from the first distillation zone 30 by a line 32 and such that substantially all of the tertiary butyl alcohol exits the column 30 through the line 34. As a consequence, the first distillation fraction 32 taken overhead from the distillation zone 30 will comprise substantially all of the isobutylene, methyl tertiary butyl ether and DME and some of the methanol and water charged to the first distillation zone 30. The second heavier distillation fraction 34 discharged from the first distillation zone 30 will comprise methanol, tertiary butyl alcohol and water.

The first distillation fraction 32 and a recycle fraction 72 are charged to a solvent extraction tower 50. As explained in greater detail hereafter, the recycle fraction 72 contains methyl tertiary butyl ether, DME, methanol and isobutylene. Within the solvent extraction tower 50 the hydrocarbon streams 32 and 72 are countercurrently contacted with water introduced by a water charge line 52 so that methanol can be extracted from the other hydrocarbons with water to thereby form an aqueous extract phase and a hydrocarbon raffinate phase. The efficiency of the extraction is improved by the isobutylene present in the extraction tower.

Within the methanol extraction tower 50, solvent extraction conditions are established for countercurrent solvent extraction including a ratio of hydrocarbon feed to water within the range of about 0.8 to 1.8 volumes of hydrocarbon per volume of water per hour, and more preferably, a ratio of about 1.0 to about 1.5 volumes of hydrocarbon per volume of water. Extraction conditions to be established may suitably include a temperature of about 20° to about 60° C. and more preferably, from about 30° to about 40° C., and a pressure of about 50 to 500 psia, and more preferably from about 50 to 150 psia.

As a consequence, a supernatant extract will be formed which is withdrawn from the top of the methanol solvent extraction tower 50 by line 60 leading to a second methyl tertiary butyl ether purification distillation column 62. The raffinate is discharged from the solvent extraction tower 50 by way of a bottoms charge line 64 leading to a third methyl tertiary butyl ether distillation zone 70.

Within the second methyl tertiary butyl ether purification distillation column 62, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a second lower boiling (lighter) distillation fraction 66 discharged from the second distillation zone 62 and a higher boiling (heavier) second distillation fraction 68 consisting essentially of product, namely methyl tertiary butyl ether.

The third lower boiling (lighter) distillation fraction 66 will comprise a mixture of isobutylene, DME and water and suitably may be charged to a decantation zone 80 where it can settle to form a supernatant isobutylene/DME phase withdrawn by way of a line 82 and a water phase withdrawn by way of a water discharge line 84 and suitably purged from the system. A portion of the isobutylene in the line 82 may be recycled to the methanol solvent extraction zone 50, if desired, by a suitable recycle line (not shown).

In accordance with the present invention, the isobutylene recovered from the decanter 80 is reacted with methanol in a secondary reactor to form additional methyl tertiary butyl ether. The reaction of isobutylene with methanol is exothermic and it is necessary to provide for positive control of the reaction temperature. This is accomplished in accordance with the present invention by limiting the rate at which isobutylene is charged to the secondary reactor and by diluting the charged isobutylene with a stream of cooled recycled reaction product.

Thus, about 80 to 95 wt. % of the isobutylene discharged from the decanter 80 by line 82 is recycled to the second distillation column 62, as reflux, by a line 63 and to the methanol extraction zone 50 by a suitable recycle line, not shown (see, for example, copending application Ser. No. 08/147,508, now U.S. Pat. No. 5,395,982 entitled "Continuous Isobutylene Assisted Extraction of Methanol from Methyl Tertiary Butyl Ether").

The remaining 10 to 15 wt. % of the isobutylene in line 82 is charged through line 87 to the secondary reactor 300 together with methanol charged by the line 88. The methanol should be mixed with the isobutylene in the line 87 in an amount sufficient to provide for a molar ratio of about 0.3 to about 0.8 mole of methanol per mol of isobutylene. The secondary reactor 300 may suitably contain a fixed bed of an isobutylene/methanol etherification catalyst, such as a bed of Amberlyst 15 sulfonated polystyrene-divinyl benzene copolymer acidic ion exchange resin.

Etherification reaction conditions established in the secondary reaction zone 300 may include, for example, a temperature of about 35° to about 100° C., a pressure of about 150 to 250 psia, and a flow rate of about 0.5 to 10 volumes of feed per volume of solid resin etherification catalyst per hour. As a consequence, the methanol and a portion of the isobutylene contained in the feed will be converted to methyl tertiary butyl ether.

An isobutylene conversion product 82 discharged from the secondary reactor 300 passes through heat exchanger 304 where the reaction product is cooled to a temperature of about 30° to about 100° C. About 10 to 20 mol % of the reaction product is recycled by the line 310 to the second distillation column 62. The remainder of the reaction product is recycled to the secondary reactor by the line 306 as a diluent.

The raffinate 64 charged to the third distillation zone 70 will comprise methyl tertiary butyl ether, isobutylene, dimethyl ether, methanol and water, and is suitably fractionated therein under distillation conditions including a liquid reflux temperature of about 20° to about 90° C., and more preferably from about 30° to about 60° C. and a reboiler temperature of about 80° to about 120° C., and more preferably from about 105° to about 115° C., and a pressure of about 15 to about 60 psia, and more preferably from about 40 to about 50 psia, to form a third lower boiling (lighter) distillation fraction 71 comprising methyl tertiary butyl ether, dimethyl ether, etc., which may suitably be partially liquified in heat exchanger 74 and then charged to surge drum 76 from which the dimethyl ether may be removed by line 79 leading from condenser/fractionator 78. The removal of the dimethyl ether is disclosed and described in greater detail in Hwan U.S. Pat. No. 5,354,912, filed Jun. 1, 1993, and entitled "Method for the Removal of Dimethyl Ether from Methyl Tertiary Butyl Ether". The liquified portion of the third lighter distillation fraction 71, mostly methyl tertiary butyl ether, is discharged from the surge drum 76 by a line 77. A portion of the liquid in the line 77 is returned to the third distillation column 70 as reflux by a line 73. The remaining portion of the third lighter distillation fraction 71 is recycled to the methanol extractor 50 by a line 72.

A third higher boiling (heavier) distillation fraction comprising water and methanol is discharged from the third distillation zone 70 by a line 75 leading to a fourth distillation zone 90. The third heavier distillation fraction 75 charged to the fourth methanol distillation zone 90 is fractionated therein under distillation conditions which may suitably include a liquid reflux temperature of about 20° to about 80° C., and more preferably from about 30° to about 60° C., a reboiler temperature of about 100° to about 140° C. and more preferably from about 110° to about 120° C., and a pressure of about 15 to about 60 psia, and more preferably from about 20 to about 30 psia, into a fourth lower boiling (lighter) distillation fraction 92 which suitably may be recycled to the methanol charge line 12. A fourth lower boiling (heavier) distillation fraction consisting essentially of water is discharged from the fourth methanol distillation zone 90 by way of a line 94 and may be discharged from the system.

The first higher boiling (heavier) distillation fraction 34 discharged from the first MTBE distillation zone 30 is charged to a fifth tertiary butyl alcohol recovery distillation zone 100 where it is fractionated under distillation conditions including a liquid reflux temperature of about 80° to about 170° C., and more preferably about 100° to about 150° C., and a reboiler temperature of about 100° to about 190° C., more preferably about 170° to about 180° C., and at a pressure of about 15 to about 190 psia, and more preferably about 110 to about 160 psia, into a fifth lower boiling (lighter) distillation fraction comprising mostly tertiary butyl alcohol and methanol that is discharged in the fifth distillation zone 100 by a line 102 leading to the tertiary butyl alcohol charge line 16 for the primary reactor 10. A fifth higher boiling (heavier) distillation fraction comprising a water fraction discharged from the distillation zone 100 by a line 106.

Having thus described our invention, what is claimed is:

1. A method comprising the steps of:
   a. charging a mixture of methanol and tertiary butyl alcohol in the molar ratio of about 0.5 to 4 moles of methanol per mole of tertiary butyl alcohol to an etherification reaction zone containing a bed of an etherification catalyst under reaction conditions including a pressure of about 30 to about 500 psia, a temperature of about 90° to about 140° C. and a flow rate of about 0.5 to about 20 volumes of feed mixture per volume of etherification catalyst per hour to thereby form a reaction product comprising unreacted methanol, unreacted tertiary butyl alcohol, water, isobutylene, DME and methyl tertiary butyl ether;
   b. charging the reaction product to a first methyl tertiary butyl ether recovery distillation zone and separating it therein into a first lower boiling (lighter) distillation fraction comprising isobutylene, DME, methanol, water and methyl tertiary butyl ether and a first higher boiling (heavier) distillation fraction comprising methanol, tertiary butyl alcohol and water;
   c. charging the first lower boiling (lighter) distillation fraction to a methanol solvent extraction zone and countercurrently contacting it therein with water in the ratio of about 1 to about 10 volumes of the first lighter distillation fraction per volume of water per hour under extraction conditions including a temperature of about 20° to about 60° C. and a pressure of about 50 to about 500 psia to thereby provide an overhead extract comprising isobutylene, DME, water and methyl tertiary butyl ether and a raffinate comprising methanol, MTBE, isobutylene, dimethyl ether and water;
   d. charging the extract to a second methyl tertiary butyl ether purification distillation zone and separating it therein into a second lower boiling (lighter) distillation fraction comprising isobutylene, DME and water and a second higher boiling (heavier) distillation fraction comprising methyl tertiary butyl ether;
   e. charging the second lower boiling (lighter) distillation fraction to a decantation separation zone and separating it therein into an isobutylene fraction and a water fraction;
   f. charging at least a portion of the isobutylene fraction and added methanol to an isobutylene conversion reaction zone in the molar ratio of about 0.3 to about 0.8 mole of methanol per mol of isobutylene and contacting them therein with a solid resin etherification catalyst under conversion conditions including a temperature of about 35° to about 100° C., a pressure of about 150 to about 250 psia and a flow rate of about 0.5 to about 10 volumes of total reactor feed per volume of solid resin etherification catalyst per hour to thereby convert the methanol and a portion of the isobutylene and to methyl tertiary butyl ether and form an isobutylene conversion product comprising methyl tertiary butyl ether, unreacted isobutylene, less than 0.5 wt. % of methanol, DME, tertiary butyl alcohol and water; and
   g. recycling said isobutylene conversion product to said second methyl tertiary butyl ether purification distillation zone.

2. A method comprising the steps of:
   a. charging a mixture of methanol and tertiary butyl alcohol in the molar ratio of about 0.7 to 4 moles of methanol per mole of tertiary butyl alcohol to an etherification reaction zone containing a bed of an etherification catalyst under reaction conditions including a pressure of about 30 to about 500 psia, a temperature of about 90° to about 140° C. and a flow rate of about 0.5 to about 20 volumes of feed mixture per volume of etherification catalyst per hour to thereby form a reaction product comprising unreacted methanol, unreacted tertiary butyl alcohol, water, isobutylene, DME and methyl tertiary butyl ether;
   b. charging the reaction product to a first methyl tertiary butyl ether recovery distillation zone and separating it therein into a first lower boiling (lighter) distillation fraction comprising isobutylene, DME, methanol, water and methyl tertiary butyl ether and a first higher boiling (heavier) distillation fraction comprising methanol, tertiary butyl alcohol and water;
   c. charging the first lower boiling (lighter) distillation fraction to a methanol solvent extraction zone and countercurrently contacting it therein with water in the ratio of about 1 to about 10 volumes of the first lighter distillation fraction per volume of water per hour under extraction conditions including a temperature of about 20° to about 60° C. and a pressure of about 50 to about 500 psia to thereby provide an overhead extract comprising isobutylene, DME, water and methyl tertiary butyl ether and a raffinate comprising methanol, MTBE, isobutylene, dimethyl ether and water;
   d. charging the extract to a second methyl tertiary butyl ether purification distillation zone and separating it therein into a second lower boiling (lighter) distillation fraction comprising isobutylene, DME and water and a second higher boiling (heavier) distillation fraction comprising methyl tertiary butyl ether;
   e. charging the second lower boiling (lighter) distillation fraction to a decantation separation zone and separating it therein into an isobutylene fraction and a water fraction;
   f. charging at least a portion of the isobutylene fraction and added methanol to an isobutylene conversion reaction zone in the molar ratio of about 0.3 to about 0.8 mole of methanol per mol of isobutylene and contacting them therein with a solid resin etherification catalyst under conversion conditions including a temperature of about 35° to about 100° C., a pressure of about 150 to about 250 psia and a flow rate of about 0.5 to about 10 volumes of total reactor feed per volume of solid resin etherification catalyst per hour to thereby convert the methanol and a portion of the isobutylene and to methyl tertiary butyl ether and form an isobutylene conversion product comprising methyl tertiary butyl ether, unreacted isobutylene, less than 0.5 wt. % of methanol, DME, tertiary butyl alcohol and water;
   g. recycling said isobutylene conversion product to said second methyl tertiary butyl ether purification distillation zone;

h. continuously charging the raffinate to a third methyl tertiary butyl ether distillation zone and separating it therein into a third lower boiling (lighter) distillation fraction comprising methyl tertiary butyl ether, methanol, isobutylene and dimethyl ether and a third higher boiling (heavier) distillation fraction comprising methanol and water;

i. charging the third higher boiling (heavier) distillation fraction to a fourth methanol recovery distillation zone and separating it therein into a fourth lower boiling (lighter) distillation fraction comprising methanol and an fourth higher boiling (heavier) distillation fraction comprising water; and j. charging the first higher boiling (heavier) distillation fraction to a fifth tertiary butyl alcohol recovery distillation zone and separating it therein into a fifth lower boiling (lighter) distillation fraction comprising tertiary butyl alcohol and a fifth higher boiling (heavier) distillation fraction comprising water.

3. A method as in claim 2 wherein the fourth lower boiling (lighter) methanol fraction and the fifth lower boiling (lighter) tertiary butyl alcohol fraction are recycled to the methyl tertiary butyl ether etherification reaction zone.

* * * * *